United States Patent [19]
Ein-Gal

[11] Patent Number: 5,879,281
[45] Date of Patent: Mar. 9, 1999

[54] STEREOTACTIC RADIOSURGERY

[76] Inventor: Moshe Ein-Gal, 30 Azar Street, Ramat Hasharon 47203, Israel

[21] Appl. No.: 753,822

[22] Filed: Dec. 2, 1996

[51] Int. Cl.$^6$ ....................................................... A61B 6/00
[52] U.S. Cl. .................................................................. 600/1
[58] Field of Search .................................... 600/1–8, 427, 600/429, 417; 378/65; 250/363.02

[56] References Cited

U.S. PATENT DOCUMENTS

| | | |
|---|---|---|
| 4,583,537 | 4/1986 | Derechinsky et al. . |
| 5,250,019 | 10/1993 | McGinley .................................... 600/1 |
| 5,291,404 | 3/1994 | Kurokawa et al. ......................... 600/1 |
| 5,452,720 | 9/1995 | Smith et al. ................................ 600/1 |
| 5,538,494 | 7/1996 | Matsuda ..................................... 600/1 |

OTHER PUBLICATIONS

Ervin B. Podgorsak, Physics For Radiosurgery With Linear Accelerators, Stereotactic Radiosurgery—Neurosurgery Clinics of North America, vol. 3, No. 1, Jan. 1992, pp. 9–50.

Jacob I. Fabrikant, et al., Charged–Particle Radiosurgery For Intracranial Vascular Malformations, Stereotactic Radiosurgery—Neurosurgery Clinics of North America, vol. 3, No. 1, Jan. 1992, pp. 99–107.

L. Dade Lunsford, et al., General Introduction: History of Radiosurgery, McGraw–Hill, 1993, pp. 1–15.

*Primary Examiner*—John P. Lacyk
*Assistant Examiner*—Samuel Gilbert
*Attorney, Agent, or Firm*—Ladas & Parry

[57] ABSTRACT

A positioning system for use in radiosurgery including a frame rigidly attachable to a part of a patient, a positioner operative to move the frame together with the part of the patient rigidly attached thereto, in at least one of six degrees of freedom, sensing apparatus operative to measure position and orientation of the frame with reference to a center of rotation, a motion controller operative to control the position and the orientation of the frame relative to the center of rotation in a time domain according to a predetermined formula.

10 Claims, 8 Drawing Sheets

STEREOTACTIC RADIOSURGERY

FIELD OF THE INVENTION

The present invention relates to radiosurgery generally, and particularly to stereotactic radiosurgery.

BACKGROUND OF THE INVENTION

Stereotactic radiosurgery provides a dose of radiation in a target volume in a patient. The target is irradiated at a multiplicity of orientations with finely collimated beams.

The use of stereotactic radiosurgery to render tissue necrotic is well established and various systems are currently used for stereotactic radiosurgery. The prior art recognizes the need to confine radiation as much as possible to the target volume being treated. Generation of a desired dose pattern at the target volume is the objective of a treatment plan which takes into account limitations of the particular radiosurgical system used. Typical types include a Gamma Unit which utilizes a multiplicity of Cobalt-60 sources arranged on a spherical surface, a linear accelerator (LINAC) which utilizes a photon beam source mounted on a rotating gantry, and a stationary generator for a beam of charged particles. These radiosurgical systems, as well as associated methods, characteristics and performances are described in various publications, e.g., in *Stereotactic Radiosurgery*, Alexander E. et al., McGraw-Hill, 1993; and in *Neurosurgery Clinics of North America*, vol. 3, no. 1, Lunsford L. D. (editor), W. B. Saunders Co., Jan. 1992.

Treatment planning capabilities include a selection of a dose level to the target, a choice of collimators for beam shaping and a determination of beam orientations at which radiation is applied to the target volume. In order to reduce the dose deposited in healthy tissue outside the target volume, it is generally desirable to spread beam orientations over a wide range.

The prior art describes beam orientations of the Gamma Unit as being fixed relative to the stationary unit. The orientation of the beam with respect to the target may be determined only by selecting the initial elevation angle of the patient's head relative to the unit. Radiation intensities and exposure times of all unplugged beams are identical for all orientations. Dose patterns may be shaped only by the elimination of selected beams through plugging the corresponding collimators prior to treatment.

A typical implementation of LINAC scanning involves rotating the LINAC gantry about its horizontal axis which orthogonally intersects the beam and the target volume at an isocenter. Such rotation causes a beam of radiation to trace an arc on a sphere surrounding the target. A multiplicity of non co-planar arcs is produced by consecutive gantry rotations, each one associated with an increment of the azimuthal orientation of the patient. The number of arcs is typically between 4 and 11. The beam intensity for each arc stays constant throughout the continuous arc irradiation. The heavy rotating gantry is associated with added expense and reduced accuracy.

Another prior art implementation of LINAC beam scanning is by rotating the patient about a vertical axis which intersects the target and irradiating with a beam which is angled with respect to the axis. Each such rotation is geometrically equivalent to the beam forming a conical surface of radiation. Incrementing the beam slant angle between consecutive rotations produces a multiplicity of coaxial conical radiation surfaces having the target in the focus. Here too, the beam intensity for each conical scan stays constant throughout the irradiation.

Yet another prior art implementation of LINAC beam scanning is by simultaneous rotation of the LINAC gantry and of the patient turntable. The orthogonal axes of rotation intersect the radiation beam at an isocenter coinciding with the target. The rotational speed about each axis is constant. The beam intensity, however, remains constant throughout the continuous irradiation. The heavy rotating gantry is associated with added expense and reduced accuracy.

Charged particles stereotactic radiosurgery uses a different approach. Since the horizontal radiation beam is stationary, beam orientations are obtained by incrementing the azimuthal orientation of the patient as well as the roll angle of the patient about a longitudinal horizontal axis. The axes of rotation intersect the radiation beam orthogonally at an isocenter coinciding with the target. Irradiation is discrete (i.e. non-continuous) from a small number of orientations. Time consuming positioning of the patient is required for each such orientation, thus preventing the use of a large number of orientations.

SUMMARY OF THE INVENTION

The present invention seeks to provide improved apparatus and techniques for radiosurgery which represent a radical departure from the prior art.

The present invention provides a treatment modality utilizing any conventional or other radiation source and introduces treatment planning options and parameters which are not reflected in the prior art.

In the present invention, in contrast with the prior art, a large number of orientations may be used and the dose delivered from each orientation is controllable. Unlike the prior art, a continuous orientations scan and dose control may be implemented utilizing a radiation source which is stationary during irradiation.

The present invention provides apparatus for selectively irradiating a target volume of tissue within a patient. A target is identified in a patient and a desired radiation dose pattern for therapeutic irradiation of the target volume is selected.

A collimator is selected in accordance with the treatment plan. A radiation source, such as a LINAC, heavy particle generator or cobalt-60 source, emits a radiation beam through the selected collimator. The collimated radiation source is positioned at predetermined orientations relative to the target volume so that the desired radiation dose to the target volume is achieved in increments from different beam paths.

The positioning of the collimated radiation beam relative to the target volume is achieved by means of a positioner attached to an immobilizing device, such as a stereotactic frame, which is in turn rigidly attached to the patient. The positioner moves and rotates the patient azimuthally and elevationally relative to the radiation beam during irradiation.

The positioner comprised in the present invention permits the positioning of the target tissue volume in different orientations relative to the radiation beam by rotating the patient azimuthally and elevationally relative to the radiation beam during irradiation. This permits the implementation of more versatile and varied irradiation plans than are available in the prior art.

As distinguished from the prior art, the present invention includes a motion controller which permits control over the dwell time of the irradiation from each orientation relative to the target volume. This provides the flexibility of delivering different doses of radiation from different orientations.

During radiation treatment, there may be varying beam attenuations caused by different tissue volumes in the beam path intervening between the radiation source and the target volume. The ability to vary the doses of radiation from different orientations compensates for the varying beam attenuations.

The ability to vary the time dwell time of the radiation beam at different orientations relative to the target volume facilitates the calculation and implementation of more versatile and varied radiation plans than are available in the prior art.

There is thus provided in accordance with a preferred embodiment of the present invention, a positioning system for use in radiosurgery including a frame rigidly attachable to a part of a patient, a positioner operative to move the frame together with the part of the patient rigidly attached thereto, in at least one of six degrees of freedom, sensing apparatus operative to measure position and orientation of the frame with reference to a center of rotation, a motion controller operative to control the position and the orientation of the frame relative to the center of rotation in a time domain according to a predetermined formula.

In accordance with a preferred embodiment of the present invention, the positioner is operative to rotate the frame and part of the body attached thereto around two axes of rotation, and wherein the first axis of rotation is generally perpendicular to the second axis of rotation.

There is also provided in accordance with a preferred embodiment of the present invention, an irradiating system for use in radiosurgical treatment including a source of radiation arranged to produce a radiation beam operative to irradiate a target volume in a patient and a positioning system as described hereinabove.

In accordance with a preferred embodiment of the present invention, the irradiating system also includes a beam controller for controlling the intensity of the radiation beam according to the position and the orientation of the frame.

The source of radiation is preferably a linear accelerator (LINAC).

There is also provided in accordance with a preferred embodiment of the present invention, a method for radiosurgical treatment of a patient including the steps of:

selecting a set of orientations of radiation beams operative to irradiate a target volume in the patient;

calculating a corresponding set of dose quotas delivered by each radiation beam at each orientation, wherein an accumulation of the dose quotas provides a desired dose pattern in and around the target volume;

determining for each dose quota a corresponding radiation intensity and exposure time which together produce the dose quota; and irradiating the target volume from each orientation according to each corresponding radiation intensity and exposure time.

In accordance with a preferred embodiment of the present invention, the method further includes providing an irradiating system, as described above, wherein the source of radiation is substantially stationary during irradiation, positioning the frame and the part of the patient rigidly attached thereto such that the target volume of the patient substantially coincides with the center of rotation of the positioning system, and using the positioning system to move the target volume according to the set of orientations of radiation beams while irradiating the target volume according to the corresponding radiation intensity and exposure time.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
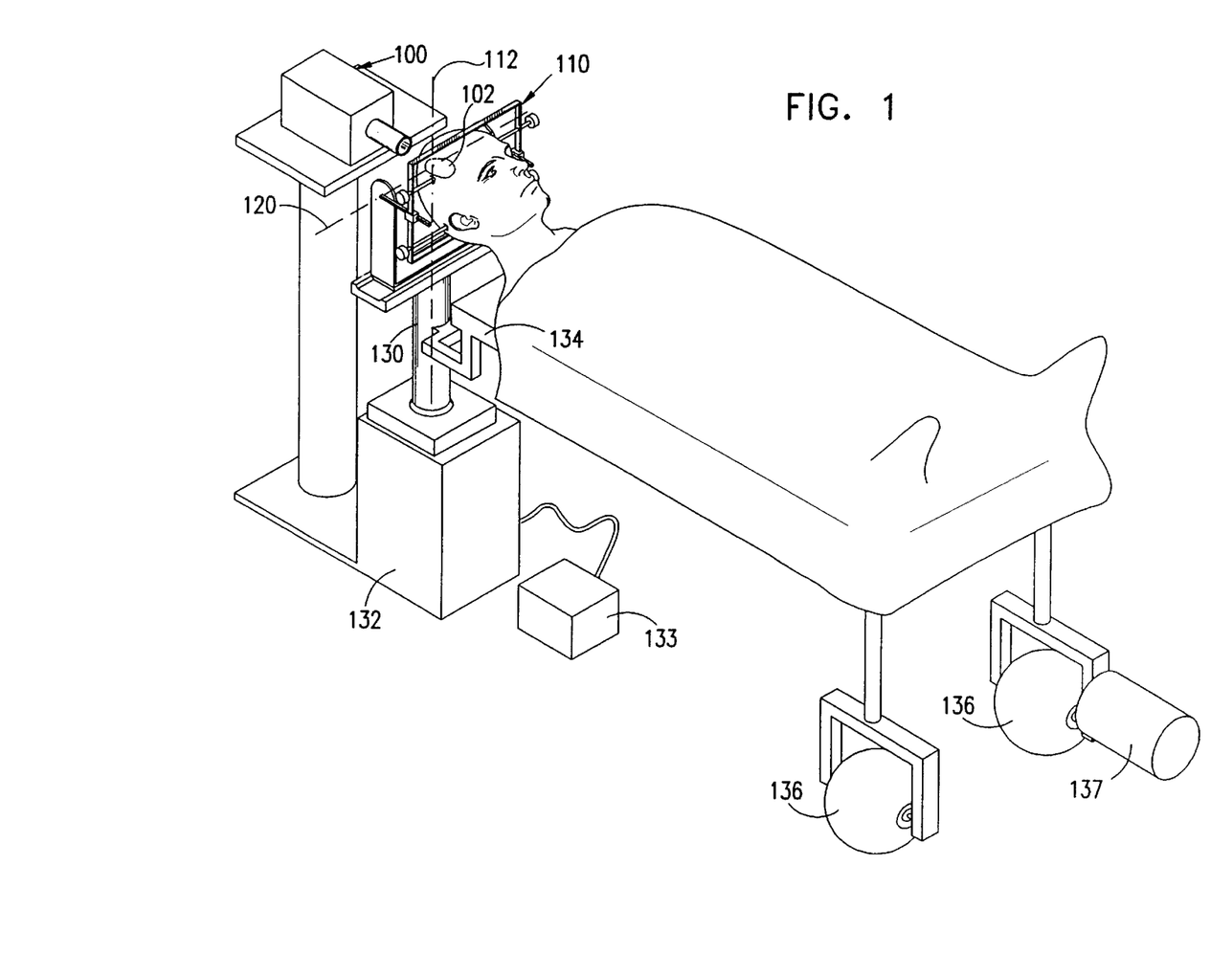
FIG. 1 is a simplified pictorial illustration of treatment of a patient using apparatus constructed and operative in accordance with a preferred embodiment of the present invention.

Reference is now made to FIG. 1, which is a simplified pictorial illustration of treatment of a patient using apparatus constructed and operative in accordance with a preferred embodiment of the present invention. Preferably an interchangeable collimator radiation generator 100, is employed to direct a beam of radiation onto a target location 102 in a patient's head.

In the present embodiment, the patient's head is securely and precisely held in position preferably by means of a stereotactic frame assembly 110, such that the target location 102 lies along a vertical axis 112, about which the entire patient is rotatable. The stereotactic frame assembly 110 defines an elevation axis 120, which intersects the vertical axis 112 at the target location 102.

The stereotactic frame assembly 110 is mounted on a post 130 which is aligned along and rotatable about axis 112. Post 130 is translatable in a plane perpendicular to axis 112, and is also selectably raisable and lowerable along axis 112, by means of an X-Y-Z translator 132. The motion of translator 132 is preferably controlled in a closed control loop by a motion controller 133 and appropriate sensors (not shown). Fixedly mounted onto post 130 is a patient support platform 134 which is provided with wheeled supports 136 at an end thereof opposite to post 130. An azimuth motor 137 may be mounted on one of the supports 136 for rotating platform 134 about axis 112.

Figure 2A:
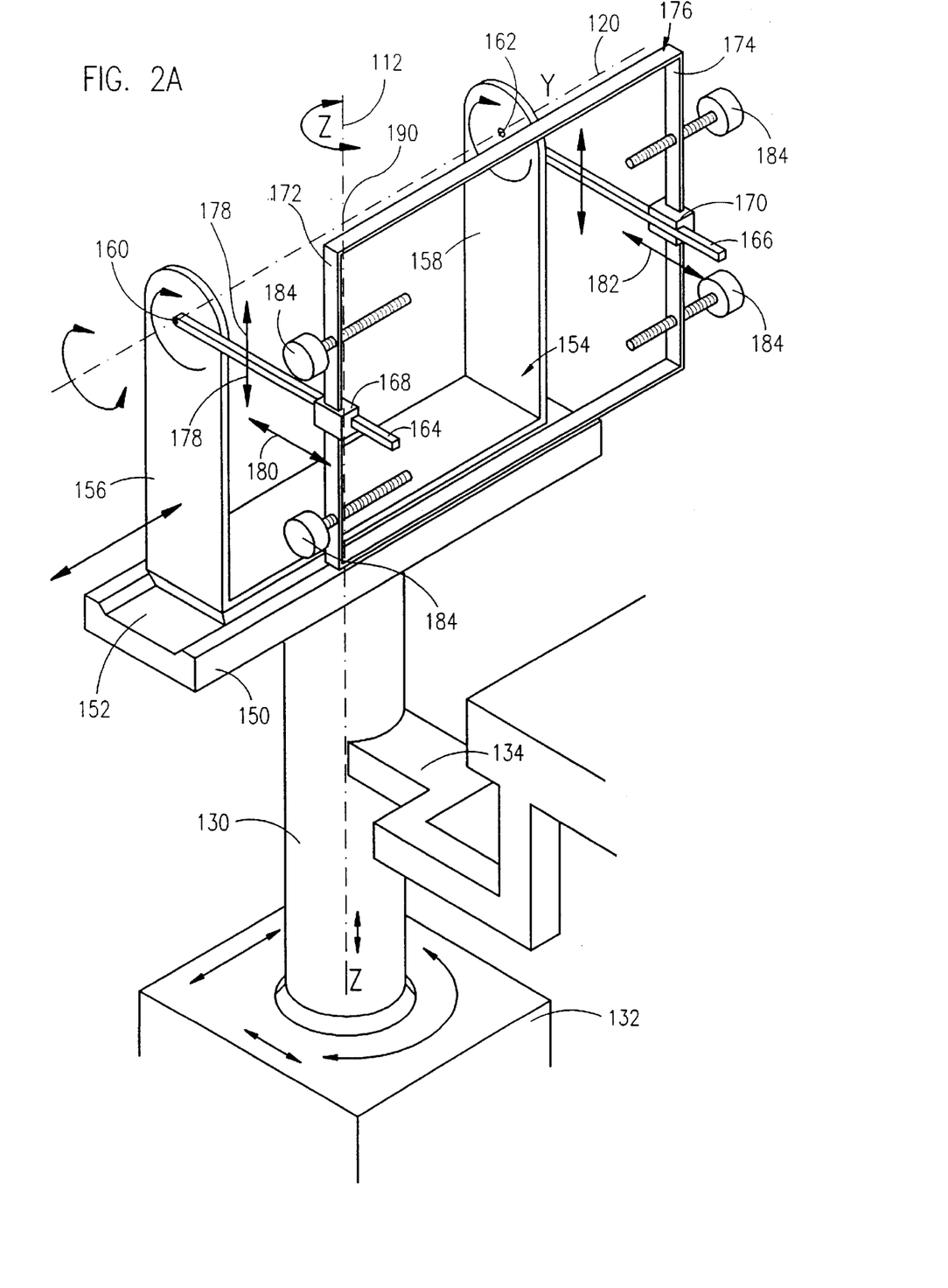
FIG. 2A is a simplified pictorial illustration of part of the apparatus of FIG. 1.

Referring now additionally to FIG. 2A, it is seen that the stereotactic frame assembly 110 comprises a generally horizontal base member 150 which is fixedly mounted onto post 130 and is translatable and rotatable together therewith. Horizontal base member 150 is formed with a track 152 along which a support element 154 is selectably displaceable in one dimension along the track. The elevation axis 120 is defined with respect to element 154 and intersects a pair of upstanding arms 156 and 158 thereof at locations 160 and 162 respectively.

A pair of pivot arms 164 and 166 are pivotably mounted onto upstanding arms 156 and 158 at locations 160 and 162 respectively. Slidably mounted onto each of pivot arms 164 and 166 are respective mounting sliders 168 and 170. Slidably mounted onto mounting sliders 168 and 170 are respective side portions 172 and 174 of a head mounting frame 176. Head mounting frame 176 is preferably slidable with respect to sliders 168 and 170 along an axis, indicated by arrows 178, which is perpendicular to the longitudinal axes of pivot arms 164 and 166, respectively indicated by arrows 180 and 182.

Figure 2B:
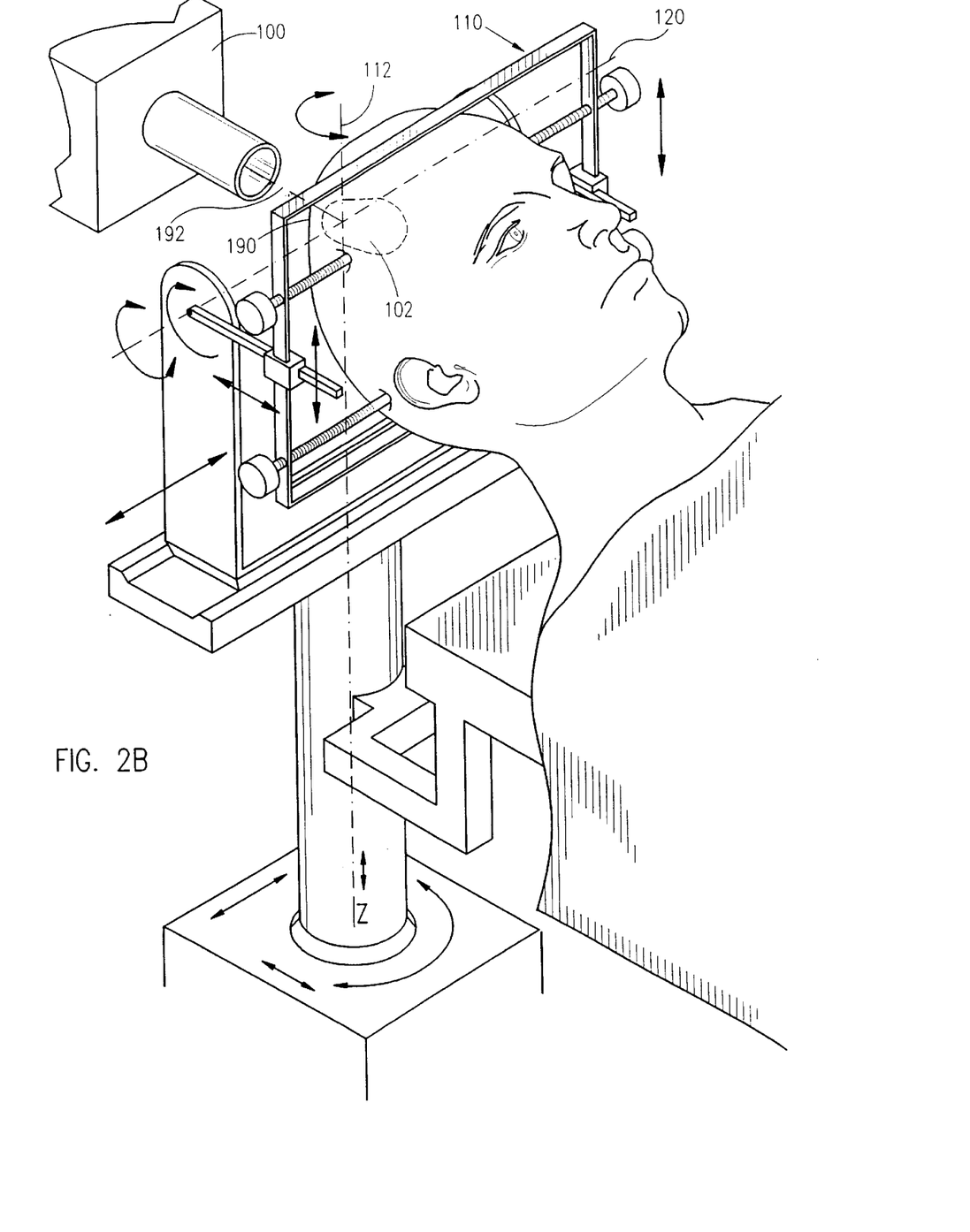
FIG. 2B is an illustration of use of the apparatus of FIG. 2A in treatment of a patient.

A plurality of mounting screws 184, which may be threadably mounted onto head mounting frame 176, are preferably employed to rigidly engage the skull of a patient and thus securely mount it with respect to frame 176, as seen in FIG. 2B. It is appreciated that stereotactic frame assembly 110 may be used not only for the skull, but for irradiating any other portion of the patient's body.

In operation, frame 176 is securely attached to the skull of a patient. The target location 102, for example, of a tumor, is determined by any suitable method, such as computerized tomography. Frame 176 is then positioned with respect to interchangeable collimator radiation generator 100 (FIG. 1) by suitable adjustment of any or all of support element 154, and mounting sliders 168 and 170, such that a center of rotation 190, located at the intersection of axes 112 and 120, is located substantially at the target location 102.

Figure 3:
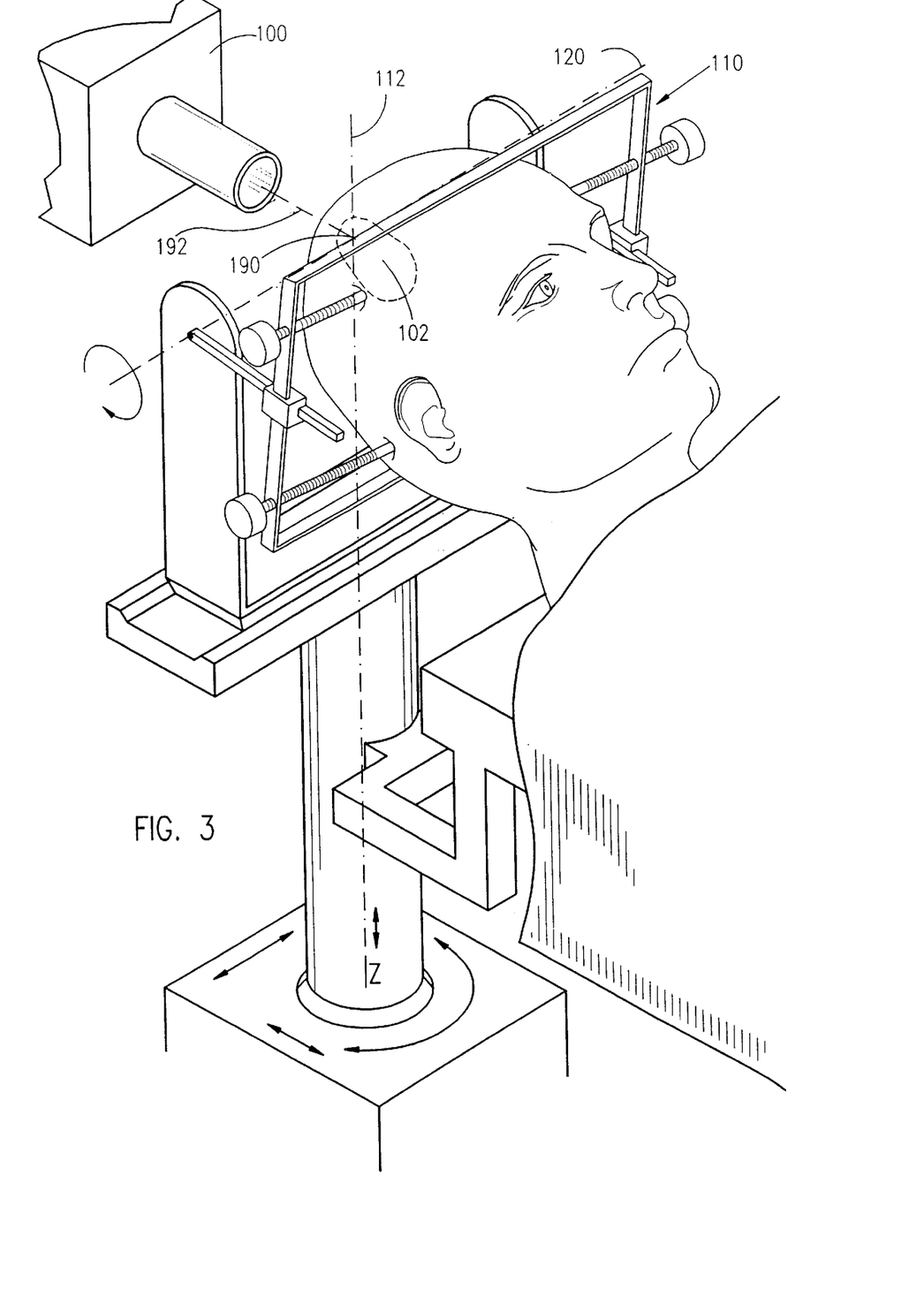
FIG. 3 is a simplified pictorial illustration of rotation of a patient about an elevation axis using apparatus illustrated in FIG. 1.

Reference is now made to FIG. 3 which is a simplified pictorial illustration of rotation of a patient about elevation axis 120 using apparatus illustrated in FIG. 1. It is noted that the location of the center of rotation 190 with respect to a beam 192, generated by interchangeable collimator radiation generator 100 and directed at center of rotation 190, remains substantially unchanged during any elevational rotation.

Figure 4:
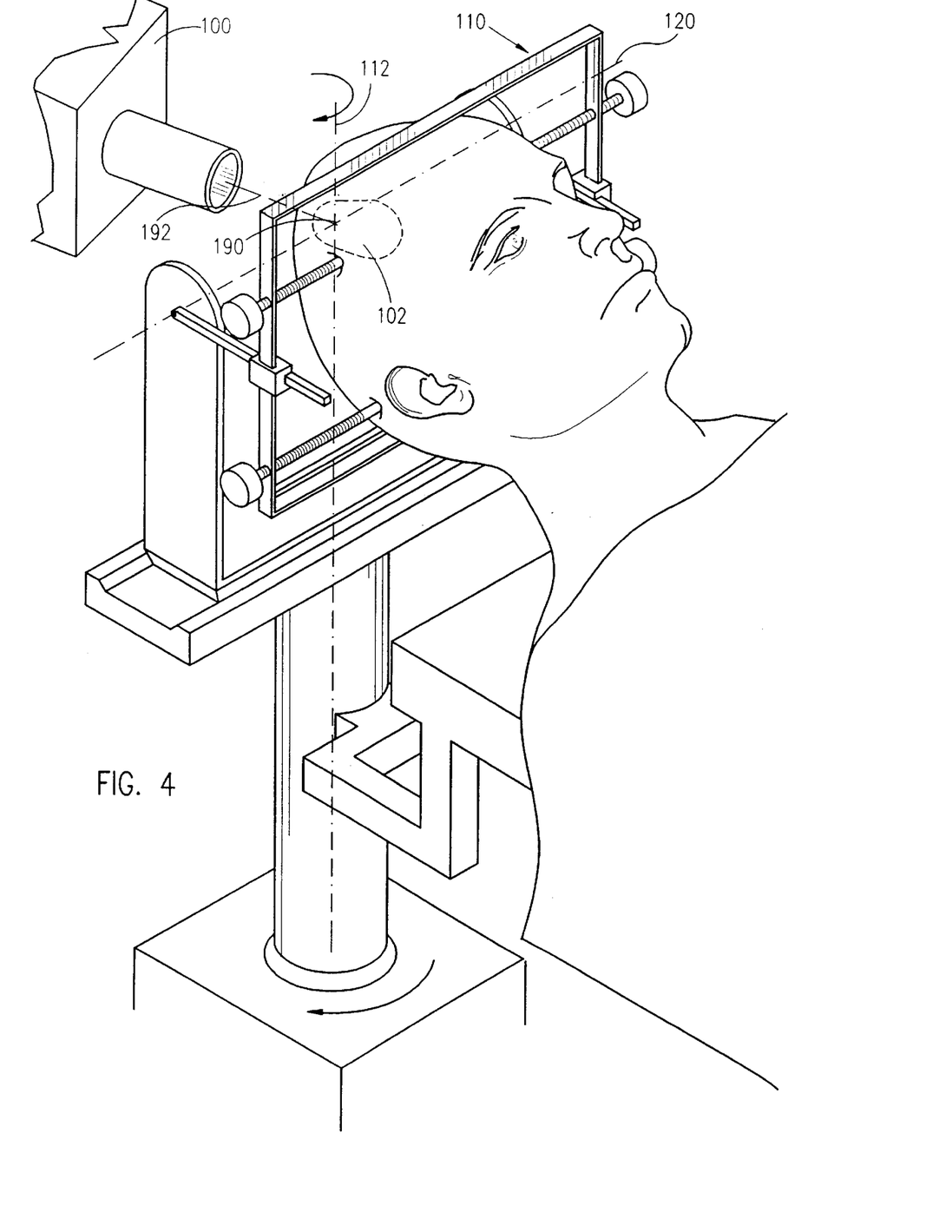
FIG. 4 is a simplified pictorial illustration of rotation of a patient about an azimuthal axis using apparatus illustrated in FIG. 1.

Reference is now made to FIG. 4 which is a simplified pictorial illustration of rotation of a patient about azimuthal axis 112 using apparatus illustrated in FIG. 1. It is noted that the location of the center of rotation 190 with respect to beam 192 remains substantially unchanged during any azimuthal rotation.

Figure 5:
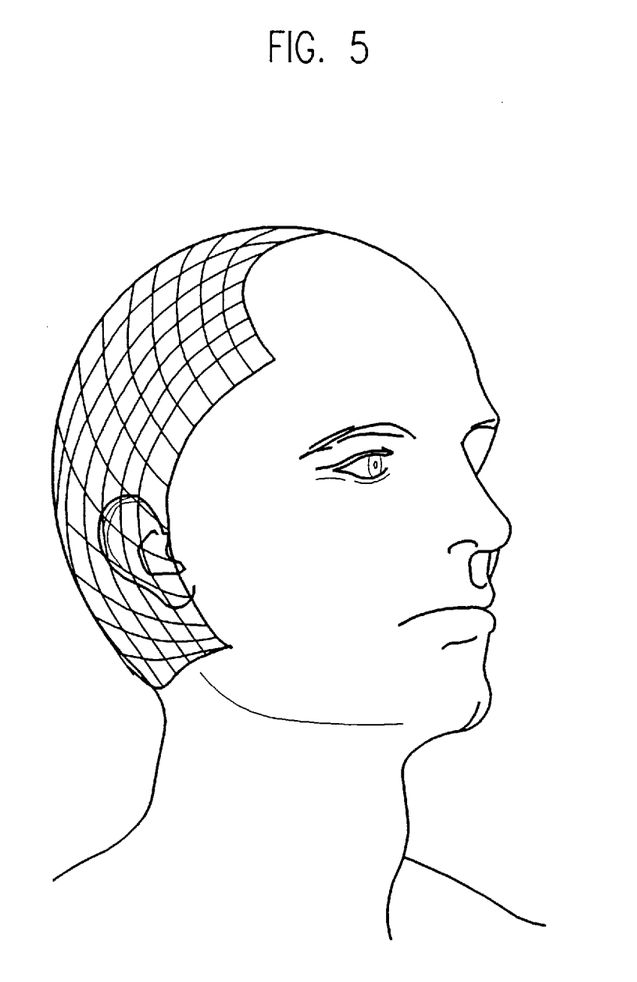
FIG. 5 is a simplified pictorial illustration of a pattern of irradiation impinging on a patient's skull, using the apparatus of FIG. 1.

Reference is now made to FIG. 5 which is a simplified pictorial illustration of an irradiation matrix projected on a patient's skull, using the apparatus of FIG. 1, and by suitable elevational and azimuthal movement of the patient. Each cell of the matrix is irradiated with a dose quota delivered by a set of radiation beams, wherein an accumulation of the dose quotas provides a desired dose pattern in and around the target volume. For each dose quota there is a corresponding pair of a radiation intensity and an exposure time, which together produce the dose quota.

Figure 6A:
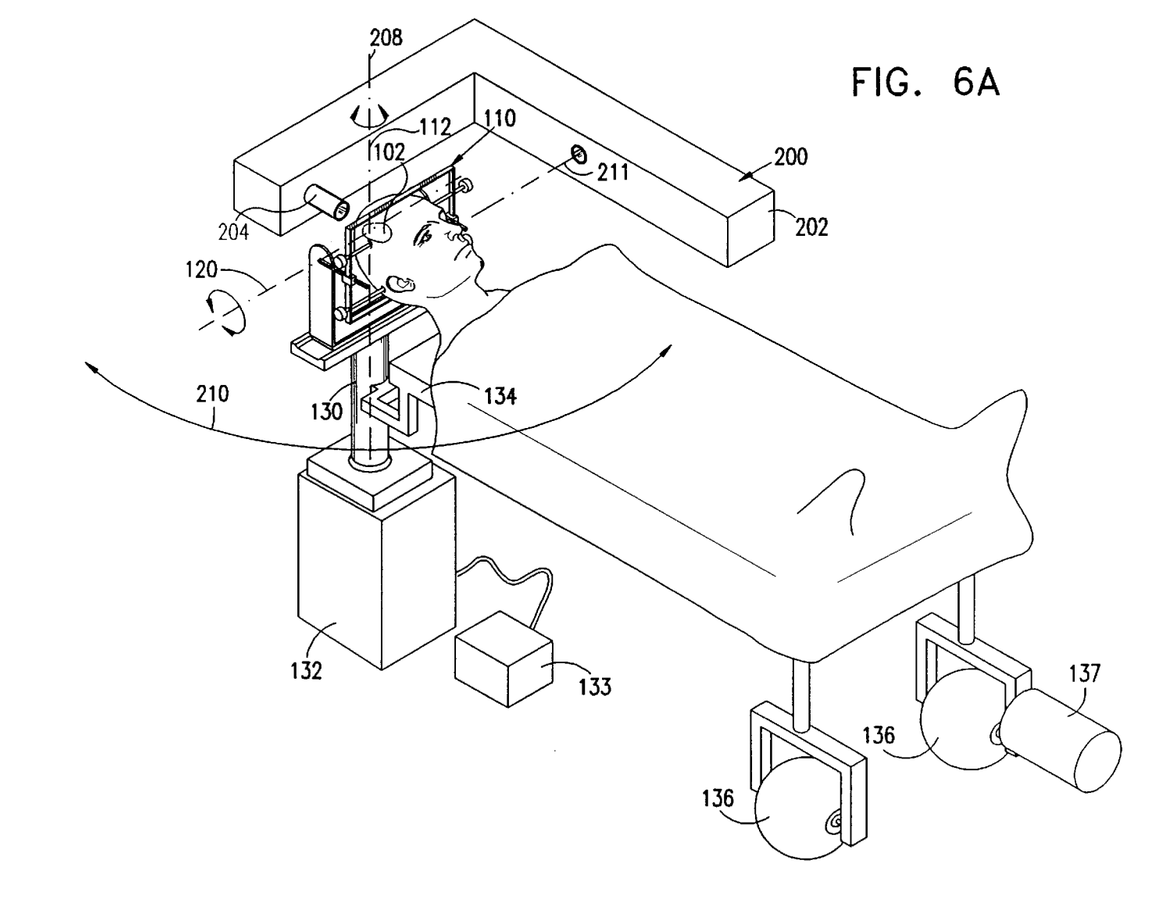
FIGS. 6A and 6B are simplified pictorial illustrations of treatment of a patient using apparatus constructed and operative in accordance with another preferred embodiment of the present invention.
Figure 6B:
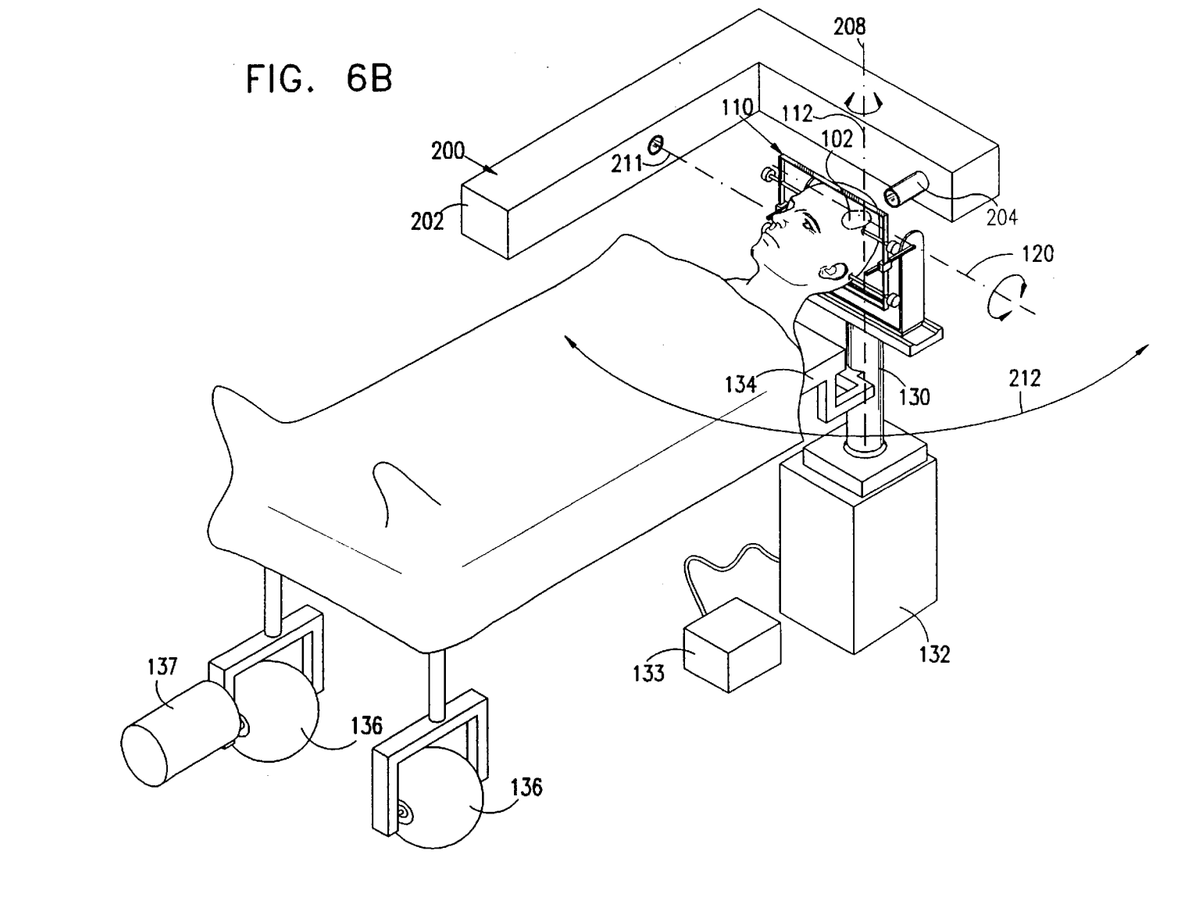

Reference is now made to FIGS. 6A and 6B which are simplified pictorial illustrations of treatment of a patient using apparatus constructed and operative in accordance with another preferred embodiment of the present invention. A linear accelerator 200 is preferably housed in a gantry 202 and is operative to irradiate a patient via a collimator 204.

The stereotactic frame assembly 110, described hereinabove with reference to FIGS. 1–4, may be used with linear-accelerator 200 to irradiate a patient. A patient may be rotated elevationally about an axis 206 and azimuthally about an axis 208, in a manner similar to that described hereinabove with reference to FIGS. 3 and 4. In FIG. 6A, azimuthal movement of the patient may be restricted generally in an angular region designated by reference numeral 210. By rotating gantry 202 about an axis 211 to the position shown in FIG. 6B, the patient may be rotated an additional angular region 212.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub combination.

It will be appreciated by persons skilled in the art that the present invention is not limited to what has been particularly shown and described hereinabove. Rather, the scope of the present invention is defined only by the claims that follow:

What is claimed is:

1. A positioning system for use in stereotactic radiosurgery comprising:

a stereotactic frame assembly for securely and precisely holding a portion of a patient such that a target location, which is located in the portion of the patient, lies along a vertical axis about which the entire patient is rotatable, said stereotactic frame assembly defining a rotation axis which intersects the vertical axis at the target location;

wherein the stereotactic frame assembly is mounted on a post which is aligned along and rotatable about the vertical axis, said post and said stereotactic frame assembly being translatable in a plane perpendicular to the vertical axis and also being selectably raisable and lowerable along the vertical axis by means of an X-Y-Z translator operatively connected to said stereotactic frame assembly;

wherein said stereotactic frame assembly comprises a base member which is fixedly mounted onto said post and is translatable and rotatable together therewith;

and wherein a support element is selectably displaceable along said base member, and wherein the rotation axis intersects a pair of upstanding arms extending from said support element;

and wherein a pair of pivot arms are pivotably mounted onto said upstanding arms, and wherein a head mounting frame is pivotally mounted to said upstanding arms.

2. The positioning system according to claim 1 and wherein a mounting slide is mounted onto each of said pivot arms, each said mounting slider sliding along a longitudinal axis of each said pivot arm, and wherein said head mounting frame is slidably mounted onto said mounting sliders, said head mounting frame being slidable with respect to said sliders along an axis, called a sliding axis, which is generally perpendicular to said longitudinal axes of said pivot arms.

3. The positioning system according to claim 1 and comprising a patient support platform which is fixedly mounted onto said post and which is provided with wheeled supports.

4. The positioning system according to claim 3 and comprising an azimuth motor mounted on one of the wheeled supports for rotating said platform about the vertical axis.

5. The positioning system according to claim 1 and wherein said base member is formed with a track along which said support element is selectably displaceable.

6. The positioning system according to claim 1 and wherein said base member is generally horizontal.

7. The positioning system according to claim 1 and wherein said pair of upstanding arms are generally perpendicular to said base member.

8. The positioning system according to claim 1 and comprising a motion controller operatively connected to said stereotactic frame assembly.

9. The positioning system according to claim 8 and wherein said motion controller is operative, upon a selection of a set of orientations of radiation beams which irradiate said target location in said patient, to calculate a corresponding set of dose quotas delivered by each said radiation beam at each said orientation, and to determine for each said dose quota a corresponding radiation intensity and exposure time which together produce a desired dose pattern.

10. A positioning system for use in stereotactic radiosurgery comprising:

a stereotactic frame assembly rigidly attachable to a part of a patient;

a positioner operative to move said stereotactic frame assembly together with said part of said patient rigidly attached thereto; and a motion controller operatively connected to said stereotactic frame assembly, wherein said motion controller is operative, upon a selection of a set of orientations of radiation beams which irradiate said target location in said patient, to calculate a corresponding set of dose quotas delivered by each said radiation beam at each said orientation, and to determine for each said dose quota a corresponding radiation intensity and exposure time which together produce a desired dose pattern.

* * * * *